US00PP27835P2

(12) United States Plant Patent
James

(10) Patent No.: US PP27,835 P2
(45) Date of Patent: Apr. 4, 2017

(54) ***VERONICA* PLANT NAMED 'NOVAVERSKY'**

(50) Latin Name: *Veronica spicata*
Varietal Denomination: Novaversky

(71) Applicant: CP DELAWARE, INC., Wilmington, DE (US)

(72) Inventor: Kenneth J. James, Colbert, GA (US)

( * ) Notice: Subject to any disclaimer, the term of this patent is extended or adjusted under 35 U.S.C. 154(b) by 0 days.

(21) Appl. No.: 14/757,206

(22) Filed: Dec. 7, 2015

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Annette Para
(74) *Attorney, Agent, or Firm* — Buchanan Ingersoll & Rooney PC

(57) ABSTRACT

The new plant resulted as a mutation of the 'Novaverpin' cultivar (U.S. Plant Pat. No. 27,748) that was discovered as a chance sport while growing in a test garden at Colbert, Ga., U.S.A. Attractive light blue blossoms are formed in abundance with a propensity to rebloom following trimming in the absence of a vernalization requirement for flowering. An attractive dense compact and mounding growth habit is displayed. The stems that bear flowers are substantially upright. The 'Novaverpin' parent displays a dissimilar light pink inflorescence coloration. The plant is well suited for providing attractive ornamentation in the landscape.

2 Drawing Sheets

Figure 1:
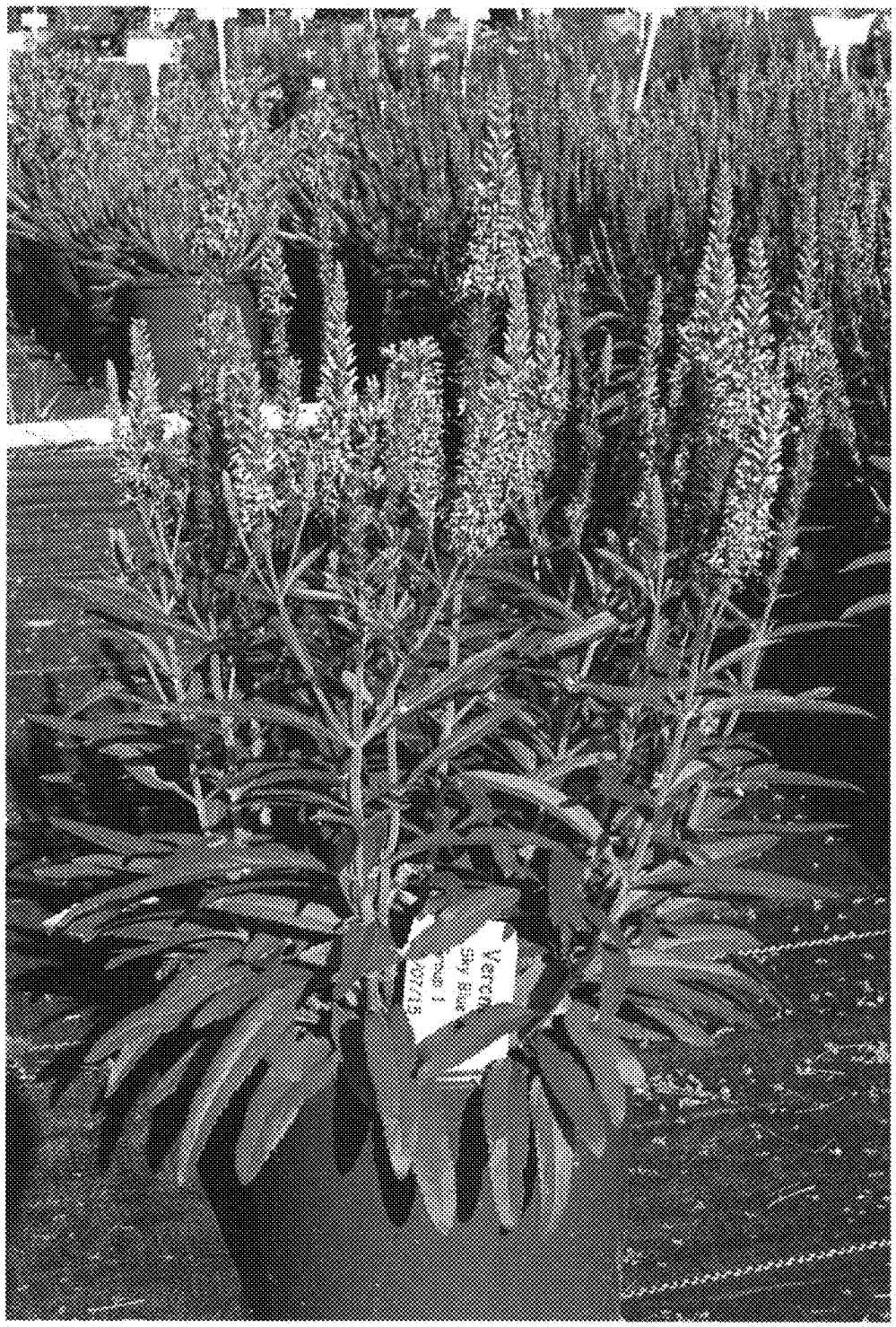

Botanical/commercial classification: *Veronica spicata /Veronica* Plant.

Varietal denomination: cv. Novaversky.

SUMMARY OF THE INVENTION

The new plant of the present invention originated as a chance sport that was discovered on Jun. 1, 2013 among plants of 'Novaverpin' *Veronica* cultivar (U.S. Plant Pat. No. 25,748) growing in a plant test area tended by man at Colbert, Ga., U.S.A. The new cultivar can be distinguished from its 'Novaverpin' parent in view of the different flower coloration as discussed hereafter. Had this plant not been discovered, identified and preserved it would have been lost to mankind.

It was found that the new *Veronica* plant of the present invention displays the following combination of characteristics:

(a) exhibits a dense compact and mounding growth habit,
(b) forms upright stems,
(c) is lacking a vernalization requirement for flowering,
(d) forms in abundance large attractive light blue inflorescence with a propensity to rebloom following trimming, and
(e) is well suited for providing attractive ornamentation in the landscape.

During observations to date, the plant has been found to be hardy in U.S.D.A. Hardiness Zone No. 6. Further hardiness trials are underway.

The new cultivar well meets the needs of the horticultural industry and can be grown to advantage as a perennial garden plant to provide colorful ornamentation. For instance, it can be grown in parks, gardens and residential settings.

Plants of the new cultivar can be readily distinguished from other *Veronica spicata* cultivars including its parent. More specifically, the 'Novaverpin' parent cultivar forms light pink blossoms instead of blossoms having the light blue coloration of the new cultivar.

The new cultivar also can be readily distinguished from the 'Rotfuchs' cultivar (non-patented in the United States). Unlike the new cultivar, the 'Rotfuchs' cultivar forms dark pink blossoms and has been found to require vernalization during observations at West Grove, Pa., U.S.A.

The new cultivar additionally can be readily distinguished from the 'Novaverlig' cultivar (U.S. Plant patent application Ser. No. 13/998,882, filed Dec. 18, 2013 through an inspection of the flowers and growth habit. More specifically, the light blue inflorescence of the new cultivar is considerably larger and the growth habit more uniform than that of the 'Novaverlig' cultivar.

The rooting of cuttings has been used to asexually propagate the new cultivar at Colbert, Ga., U.S.A. and at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novaversky', and will be marketed under the SKY BLUE MOODY BLUES Trademark.

BRIEF DESCRIPTION OF THE PHOTOGRAPHS

The accompanying photographs illustrate the new cultivar in color as nearly true as it is reasonably possible make the same in color illustrations of this nature. The plants were being grown on their own roots at West Grove, Pa., U.S.A.

FIG. 1 illustrates a specimen of a typical one-year-old flowering plant of the new cultivar while growing outdoors in a container in full sun during July 2015. The typical attractive upright dense compact mounding growth habit and large inflorescence are shown.

Figure 2:
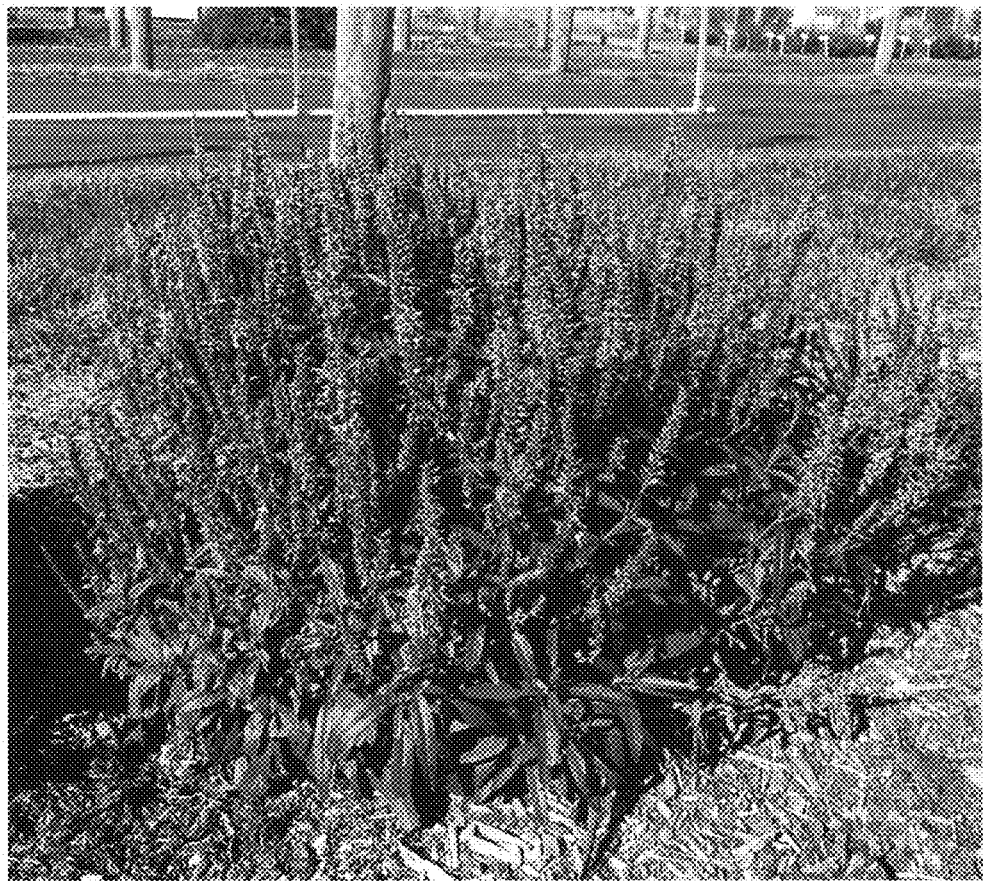

FIG. 2 further illustrates a specimen of a typical two-year-old flowering plant growing outdoors in the ground in full sun during October 2015.

DETAILED BOTANICAL DESCRIPTION

The following is a detailed description while observing one-year-old plants of the new cultivar that were produced by the rooting of cuttings. Such plants were grown in one-gallon containers outdoors at West Grove, Pa., U.S.A. The chart used in the identification of color is The R.H.S. Colour Chart (1995 Edition) of The Royal Horticultural Society, London, England. Common color terms are to be accorded their customary dictionary significance.

Botanical classification: *Veronica spicata*, cv. Novaversky.

*Parent.*—*Veronica spicata,* cv. Novaverpin.

*Plant type.*—Herbaceous perennial.

Plant:

*Growth habit.*—Substantially uniform, dense compact and mounding.

*Height.*—Approximately 28 cm on average when grown in a container.

*Spread.*—Approximately 22 cm on average when grown in a container.

*Branching.*—Commonly approximately 3 to 8 lateral stems arise from a mat of congested basal stems.

*Branching angle.*—Commonly approximately 40 degrees.

*Stem length.*—Commonly approximately 25 cm on average.

*Stem diameter.*—Commonly approximately 2 mm on average.

*Stem shape.*—Substantially round in cross-section.

*Stem color.*—Near Yellow-Green Group 147C.

*Stem texture.*—Finely pubescent surface.

*Internode length.*—Commonly approximately 2.5 cm.

*Roots.*—Fibrous network.

Foliage:

*Arrangement.*—Opposite.

*Shape.*—Obovate to elliptic.

*Apex.*—Obtuse.

*Base.*—Acuminate.

*Length.*—Commonly approximately 9 cm on average for lower leaves, and approximately 4 cm on average for upper leaves.

*Width.*—Commonly approximately 2.5 cm on average for lower leaves and approximately 1 cm on average for upper leaves.

*Texture.*—On the upper surface sparsely pubescent, and on the under surface sparsely pubescent with moderate pubescence on the veins.

*Color.*—On the upper surface near Green Group 138A, and on the lower surface near Green Group 138B.

*Margins.*—Entire and somewhat crenate.

*Venation.*—Pinnate and near Yellow-Green Group 144A in coloration.

*Fragrance.*—None noticeable.

*Petiole.*—Commonly approximately 2 cm in length on average, approximately 2 mm in diameter on average, finely pubescent, and near Yellow-Group 144C in coloration.

*Stipules.*—Absent.

Inflorescence:

*Time.*—Commonly May through July at West Grove, Pa., U.S.A. with good rebloom following trimming.

*Type.*—Raceme of single funnel-shaped flowers.

*Buds.*—Elongated ovoid, approximately 6 mm in length just before opening, approximately 1.5 mm in diameter, and near Violet-Blue Group 94B in coloration.

*Quantity.*—Free-flowering, commonly 1 to 5 flowering racemes per lateral branch, and commonly approximately 125 open flowers on average per inflorescence.

*Inflorescence length.*—Commonly approximately 12 cm on average, with a length of up to approximately 7 cm on average being observed for the 'Novaverpin' cultivar.

*Inflorescence width.*—Commonly approximately 2 cm on average.

*Flower diameter.*—Approximately 9 mm.

*Flower depth.*—Approximately 7 mm on average.

*Aspect.*—Commonly approximately 30 degrees prior to opening and substantially horizontal when fully open.

*Corolla configuration.*—Funnel-shaped with petals fused into a tube towards the base and positioned separately with up to approximately 6 in a whorl.

*Petal number.*—Four.

*Petal tube.*—Approximately 2 mm in length on average, approximately 2 mm in width on average, glabrous in texture, and near Violet-Blue Group 94C in coloration. This compares to a light pink coloration of near Red-Purple Group 69D for the 'Novaverpin' parent cultivar.

*Petal lobes.*—Approximately 5 mm in length on average, approximately 3 mm in width on average, glabrous in texture, broadly linear in configuration, entire margins, rounded apex, and near Violet-Blue Group 94B on the upper surface and near Violet-Blue Group 94C on the lower surface.

*Sepal arrangement.*—Four in number, fused at base.

*Sepal shape.*—Triangular-ovate.

*Sepal length.*—Approximately 3 mm on average.

*Sepal diameter.*—Approximately 1 mm on average.

*Sepal apex.*—Acute.

*Sepal margin.*—Entire.

*Sepal texture.*—Finely pubescent.

*Sepal color.*—Near Green Group 137B on the upper surface and near Green Group 137C on the under surface.

*Stamen number.*—Two.

*Anther shape.*—Ovoid.

*Anther length.*—Approximately 1.5 mm on average.

*Anther width.*—Approximately 0.6 mm on average.

*Anther color.*—Near Purple Group 79A.

*Filaments.*—Commonly approximately 6 mm in length on average, commonly approximately 0.5 mm in diameter on average, and near Violet-Blue Group 93D in coloration.

*Pollen.*—Present in a moderate quantity, and near Greyed-Yellow Group 162D in coloration.

*Pistil number.*—One, with stigma and style not being readily distinguishable.

*Shape.*—Filiform.

*Color.*—Near Violet-Blue Group 94C.

*Length.*—Approximately 7 mm.

*Width.*—Commonly less than 0.5 mm.

*Ovary shape.*—Rounded.

*Ovary length.*—Approximately 1.5 mm on average.

*Ovary width*.—Approximately 1 mm on average.
*Ovary color*.—Near Green Group 138B.
*Seed number*.—Commonly 4 or less.
*Seed shape*.—Ovoid and commonly with flattening.
*Seed length*.—Approximately 1 mm on average.
*Seed diameter*.—Approximately 1 mm on average.
*Seed width*.—Commonly less than 0.5 mm.
*Seed color*.—Grey-Brown Group 199B.
*Fragrance*.—None observed.
*Flower longevity*.—Approximately 7 days on the plant.
*Peduncle length*.—Approximately 1.5 cm on average.
*Peduncle diameter*.—Substantially round and approximately 1 mm on average.
*Peduncle texture*.—Finely pubescent.
*Peduncle color*.—Near Yellow-Green Group 147C.
*Pedicel length*.—Approximately 1 mm on average.
*Pedicel width*.—Commonly less than 0.5 mm.
*Pedicel texture*.—Finely pubescent.
*Pedicel color*.—Near Yellow-Green Group 147D.

Disease resistance: No particular resistance to pathogens and pests common to *Veronica* plants has been encountered during observations to date.

Plants of the 'Novaversky' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Veronica* plant having the following combination of characteristics:

(a) exhibits a dense compact and mounding growth habit,
(b) forms upright stems,
(c) is lacking a vernalization requirement for flowering,
(d) forms in abundance large attractive light blue inflorescence with a propensity to well rebloom following trimming, and
(e) is well suited for providing attractive ornamentation in the landscape;

substantially as illustrated and described.

* * * * *